(12) United States Patent
Chen et al.

(10) Patent No.: US 8,283,469 B2
(45) Date of Patent: Oct. 9, 2012

(54) PERYLENE DIIMIDE DERIVATIVE AND ORGANIC SEMICONDUCTOR ELEMENT USING THE SAME MATERIAL

(75) Inventors: Szu-Ying Chen, Taoyuan County (TW); Heng-Wen Ting, Pingtung County (TW); Tri-Rung Yew, Hsinchu (TW); Jeng-Hua Wei, Taipei (TW)

(73) Assignee: National Tsing Hua University, Hsinchu (TW)

( * ) Notice: Subject to any disclaimer, the term of this patent is extended or adjusted under 35 U.S.C. 154(b) by 314 days.

(21) Appl. No.: 12/730,542

(22) Filed: Mar. 24, 2010

(65) Prior Publication Data

US 2011/0233526 A1    Sep. 29, 2011

(51) Int. Cl.
 *C07D 471/02* (2006.01)
 *H01L 29/12* (2006.01)
(52) U.S. Cl. ................................. 546/37; 257/40
(58) Field of Classification Search ............... 546/37; 257/40
See application file for complete search history.

(56) References Cited

U.S. PATENT DOCUMENTS

| 6,806,368 B2 | 10/2004 | Wurthner et al. |
| 7,026,643 B2 | 4/2006 | Dimitrakopoulos et al. |
| 7,198,977 B2 | 4/2007 | Shukla et al. |
| 7,326,956 B2 | 2/2008 | Shukla et al. |
| 2005/0176970 A1 | 8/2005 | Marks et al. |
| 2009/0236591 A1* | 9/2009 | Konemann et al. ............ 257/40 |

OTHER PUBLICATIONS

Schmidt, R. et al.: High-performance air-stable n-channel organic thin film transistors based on halogenated perylene bisimide semiconductors. J. Am. Chem. Soc., vol. 131, pp. 6215-6228, 2009.*

* cited by examiner

*Primary Examiner* — Charanjit Aulakh
(74) *Attorney, Agent, or Firm* — Muncy, Geissler, Olds & Lowe, PLLC

(57) ABSTRACT

The present invention discloses a soluble and air-stable perylene diimide (PDI) derivative to function as an N-type organic semiconductor material. In the PDI derivative of the present invention, the core thereof is substituted by electron withdrawing groups, and the side chains thereof are substituted by benzene functional groups, whereby are promoted the solubility and air-stability of the molecule. The PDI derivative of the present invention can be used to fabricate an organic semiconductor element via a soluble process at a low temperature and under an atmospheric environment.

14 Claims, 3 Drawing Sheets

PERYLENE DIIMIDE DERIVATIVE AND ORGANIC SEMICONDUCTOR ELEMENT USING THE SAME MATERIAL

FIELD OF THE INVENTION

The present invention relates to a perylene diimide derivative, particularly to a low-temperature soluble and air-stable perylene diimide derivative. The present invention also relates to an organic semiconductor element adopting an N-type semiconductor made of the perylene diimide derivative.

BACKGROUND OF THE INVENTION

Organic semiconductor materials may be categorized into the P type and the N type. The P-type organic semiconductor materials, such as pentacene and oligothiophene, are maturer and more stable. Because of cheapness and flexibility, organic materials have been widely used in electronic elements and opto-electronic industry, such as OLED (Organic Light-Emitting Diode), OTFT (Organic Thin Film Transistor) and OFET (organic field-effect transistor). OTFT and OFET are extensively used in the solar cell industry and the flexible electronic industry. In contrast to the traditional inorganic MOS (Metal-Oxide-Semiconductor) elements, the organic semiconductor elements use organic materials to replace the traditional inorganic silicon semiconductor materials to reduce the cost and achieve a slim and flexible element.

The primary electric parameters of FET include electron mobility ($\mu$), on/off current ratio ($I_{on}/I_{off}$) and threshold voltage ($V_T$). The higher the electron mobility, the rapider the charge movement, and the faster the processing speed of the element signal. The higher the on/off current ratio is, the smaller the leakage current, and the less the power consumption. The lower the threshold voltage, the lower the voltage to drive the transistor element, and the lower the power. Organic molecules are combined to form a crystallization by a weaker force, such as hydrogen bond or van der Waals force. The overlap of the orbits of molecules is smaller. Electrons are transferred via hopping between the orbits or energy levels of molecules.

In an N-type organic semiconductor material, electron is the transferring medium. Thus, the way that molecules stacked in space is particularly important. If a molecular in the crystal has an orientation or if the molecules are stacked orderly along the direction of electron conduction, the barrier of electron hopping is decreased, and higher electron mobility is achieved. N-type organic material molecular carrying negative charge is likely to react with mist and oxygen in air and denatures. Therefore, N-type organic semiconductor materials generally have poor air-stability. After a long time of use, the electron mobility of an N-type organic semiconductor material will be decreased, and even the element itself will fail. In OFET, most metal layers are made of metals having a higher work function, such as gold (4.6 eV) and silver (4.8 eV). If an N-type organic semiconductor material has too low a work function, electrons are hard to transfer from a metal layer to the organic material layer. Therefore, LUMO (Lowest Unoccupied Molecular Orbital) of an N-type organic semiconductor material must be appropriately controlled to match the Fermi levels of the metals of the source electrode and drain electrode to prevent from a Schottky barrier therebetween and favor electron injection.

Organic semiconductor materials are traditionally fabricated with a thermal evaporation method or a vapor phase deposition method. The thermal evaporation method can fabricate an organic semiconductor material with the molecules arranged more orderly to achieve higher electron mobility. However, the thermal evaporation method needs a vacuum environment, which conflicts with the requirement of reducing the fabrication cost. Further, the organic semiconductor materials made of the thermal evaporation method also have a problem of poor air-stability. An organic semiconductor material is usually applied to a flexible substrate. The softening or cracking temperature of a flexible substrate is about 200° C. Therefore, the organic semiconductor material should be fabricated with a low-temperature method, such as the spin-coating method, the inkjet-printing method or the all-soluble method, to overcome the temperature limitation of a flexible substrate.

U.S. Pat. Nos. 7,026,643, 7,198,977, 6,806,368 and 7,326,956 respectively discloses an "Organic N-Channel Semiconductor Device of N,N' 3,4,9,10 Perylene Tetracarboxylic Diimide", "N, N'-di(phenylalky)-Substituted Perylene-Based Tetracarboxylic Diimide Compounds as N-type Semiconductor Materials for Thin Film Transistors", "Liquid Crystalline 3,4:9,10-Perylenetetacarbocylic Acid Diimides", and "Fluorine-Containing N,N'-Diaryl Perylene-Based Tetracarboxylic Diimide Compounds as N-Type Semiconductor Materials for Thin Film Transistors". The abovementioned patents respectively disclose different N-type semiconductor materials. However, all the abovementioned N-type semiconductor materials must be fabricated with the thermal evaporation method in a vacuum environment. Further, they still have the problem of poor air-stability.

SUMMARY OF THE INVENTION

One objective of the present invention is to provide an N-type organic semiconductor material, which can be dissolved in a solution and can be fabricated with a solution process in the atmospheric environment, and which has a better air-stability, whereby the fabrication cost is reduced, and whereby the characteristics thereof are stably maintained in the atmospheric environment.

To achieve the abovementioned objective, the present invention proposes a soluble air-stable perylene diimide derivative to function as an N-type semiconductor material. The perylene diimide derivative of the present invention has the following chemical structure formula:

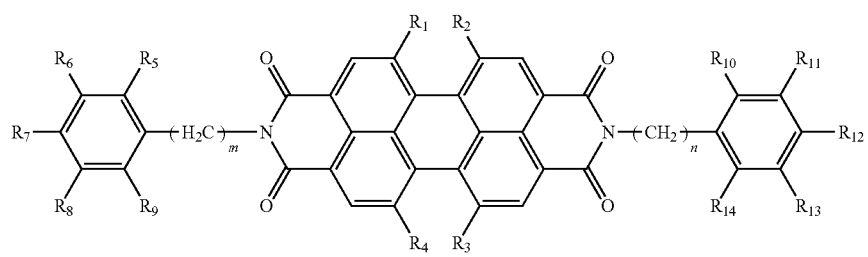

wherein m and n are respectively selected from the integers of 1-5 and independent to each other, and wherein $R_1$, $R_2$, $R_3$ and $R_4$ are respectively selected from halogens (such as fluorine and chlorine) or electron withdrawing groups, and wherein $R_5$-$R_9$ and $R_{10}$-$R_{14}$, which are respectively at two ends of the molecule, are independent to each other, and wherein at least two of $R_5$-$R_9$ are selected from a group consisting of halogens, $C_1$-$C_{20}$ fluorinated alkyl group, and $C_1$-$C_{20}$ perfluorinated alkyl radical with the rest of $R_5$-$R_9$ are hydrogens, and wherein at least two of $R_{10}$-$R_{14}$ are selected from a group consisting of halogens, $C_1$-$C_{20}$ fluorinated alkyl group, and $C_1$-$C_{20}$ perfluorinated alkyl radicals with the rest of $R_{10}$-$R_{14}$ are hydrogens.

Below, the technical contents of the present invention are described in detail in cooperation with the drawings.

BRIEF DESCRIPTION OF THE DRAWINGS

Below, the embodiments of the present invention will be described in cooperation with the following drawings.

DETAILED DESCRIPTION OF THE PREFERRED EMBODIMENTS

Figure 1:
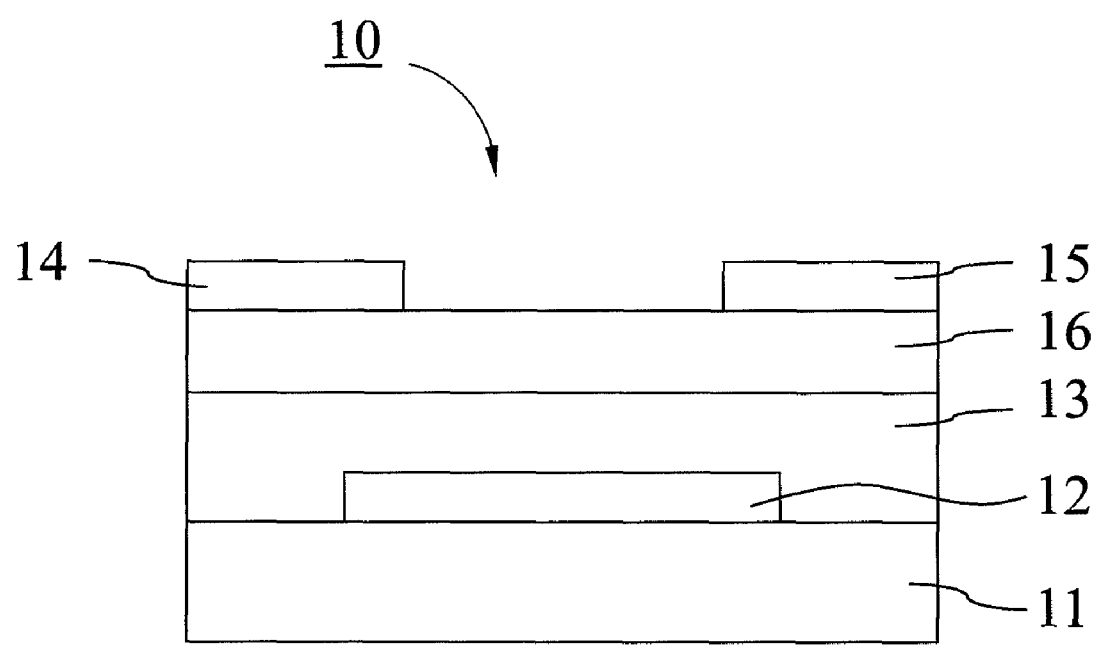
FIG. 1 is a diagram schematically showing that a PDI derivative applies to a BG-TC OTFT according to the present invention.

The present invention proposes a soluble and air-stable perylene diimide derivative to function as an N-type semiconductor material. The perylene diimide derivative of the present invention has the following chemical structure formula:

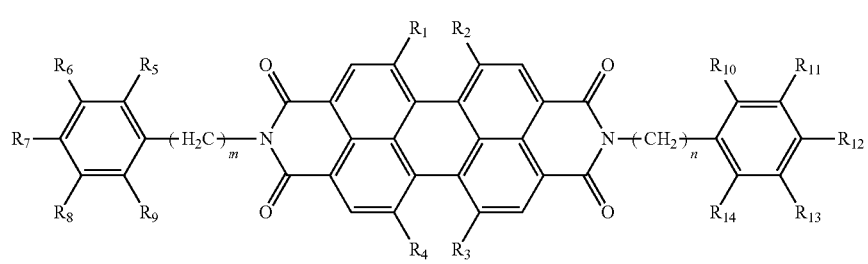

(1)

wherein m and n are respectively selected from the integers 1-5 and independent to each other, and wherein $R_1$, $R_2$, $R_3$ and $R_4$ are selected from electron withdrawing groups, and wherein $R_5$-$R_9$ and $R_{10}$-$R_{14}$, which are respectively at two ends of the molecule, are independent to each other, and wherein at least two of $R_5$-$R_9$ are selected from a group consisting of halogens, $C_1$-$C_{20}$ fluorinated alkyl group, and $C_1$-$C_{20}$ perfluorinated alkyl radical with the rest of $R_5$-$R_9$ are hydrogens, and wherein at least two of $R_{10}$-$R_{14}$ are selected from a group consisting of halogens, $C_1$-$C_{20}$ fluorinated alkyl group, and $C_1$-$C_{20}$ perfluorinated alkyl radical with the rest of $R_{10}$-$R_{14}$ are hydrogens.

In the abovementioned perylene diimide derivative, perylene diimide (PDI) functions as the backbone thereof, and the third, fourth, ninth and tenth carbon atoms of the functional groups of PDI are substituted by hydrogen atoms, and two ends of PDI are respectively connected with benzene functional groups. In one embodiment, perylene reacts with amide to form a compound, and the compound is dehydrated to generate the perylene diimide derivative of the present invention.

When halogens or electron withdrawing groups substitute the side chains ($R_1$-$R_4$) of the perylene core, the solubility of the derivative is increased, and LUMO of the molecule is also reduced. Thus is decreased the barrier of electron injection and increased the electron conductivity in the molecular structure. The electron withdrawing groups include the halogen functional groups (such as the fluorine group (—F) and the chlorine group (—Cl)) and the cyanogen group (—CN). For example, the chlorine atom has unfilled 3d orbits. Thus, electrons can be localized in the 3d orbits and would not be trapped by mist or oxygen. Therefore, better air-stability can be achieved.

When the nitrogen atoms at two sides of the side chains of PDI derivative are respectively connected with $(CH_2)_n$ and $(CH_2)_m$ and then further connected with benzene, the solubility of the entire molecule is increased. Further, the dehydration reaction is enhanced in some cases. Thus, the benzene functional groups can be easily connected to PDI derivative. If m equals to n, the symmetry of the molecules is enhanced, which favors orderly stacking of the molecule. Further, the benzene has delocalized π orbits, which favors electron conduction via hopping.

In one embodiment, at least two of five hydrogen atoms of each end of the benzene ($R_5$-$R_9$ or $R_{10}$-$R_{14}$), which are respectively at two ends of the perylene diimide derivative, are substituted by electron withdrawing groups. In such a case, LUMO of the molecule is reduced, and the solubility and air-stability of entire molecule are increased. In one embodiment, one of the substituent electron withdrawing groups is fluorine group. Fluorine is the atom having the strongest electronegativity. As fluorine atom has a very small size, it does not cause the barrier and effect the configuration of entire molecule. Fluorine substituent can increase the thermal stability of the material and enhance the effect of isolating air and mist to further promote the air-stability. In one embodiment, one of the substituent electron withdrawing groups is the fluorine group, and another substituent electron withdrawing group is a $C_1$-$C_{20}$ fluorinated alkyl group or a $C_1$-$C_{20}$ perfluorinated alkyl group. Both are electron withdrawing groups and able to increase the attraction between the molecular chain and the solvent. Thus is increased the solubility. In a preferred embodiment, the fluorine group and the $C_1$-$C_{20}$ (per)fluorinated alkyl radical are arranged at the meta positions of the benzene to form an asymmetry with respect to the nitrogen atom and increase the solubility. In some embodiments, both $R_7$ and $R_{12}$ are hydrogen atoms. In the synthesis, the lone pair electron of the amino group reacts with the oxygen atom of the perylene in side chains. In reaction, the strength of the lone pair electron of the nitrogen atom is influenced by the functional groups of the benzene. If both $R_7$ and $R_{12}$ are hydrogen atoms, the synthetic reaction is enhanced. In some cases, $R_5$-$R_9$ and $R_{10}$-$R_{14}$ substituent are symmetric, whereby the molecules can be arranged more orderly, and whereby the conduction speed of electrons is accelerated.

Embodiment

Below, an embodiment is used to demonstrate the present invention. However, the embodiment is only to exemplify the present invention but not to limit the scope of the present invention. The chemical structure formula of the perylene diimide derivative TC-PDA-F of this embodiment is

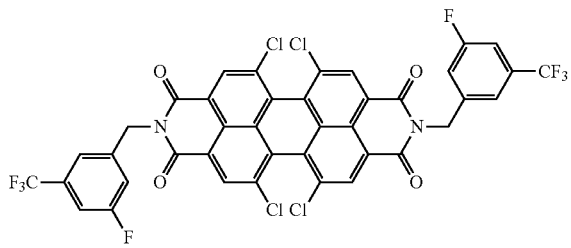

Compared with the abovementioned general formula (1), both m and n are 1 in this embodiment; $R_1$, $R_2$, $R_3$ and $R_4$ are all substituted by chlorine atoms; $R_6$ and $R_8$ are respectively substituted by F and $CF_3$; $R_{11}$ and $R_{13}$ are respectively substituted by F and $CF_3$. F and $CF_3$ are at the meta positions of the benzene. The synthetic method is as follows: prepare 1-fluoro-5-trifluoromethyl benzyl amine and 0.914 g (1.726 mmol) solution of TC-PDA (tetrachloroperylene-3,4,9,10-tetracarboxylic dianhydride) in 20 g of propionic acid solution and agitate the mixture solution for 8 hours at a temperature of 140° C.

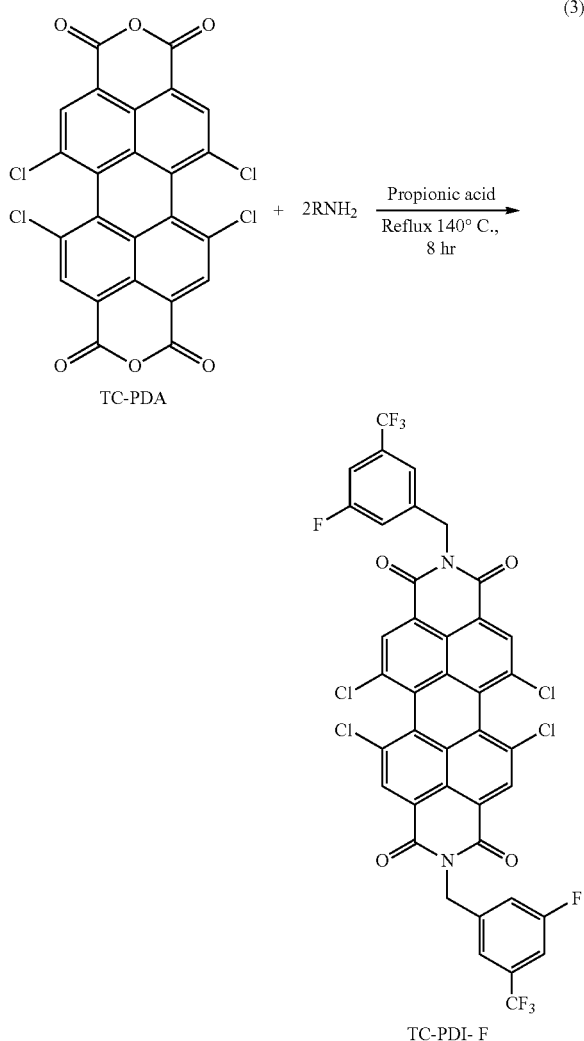

The perylene diimide derivative (TC-PDA-F) can be dissolved in an organic solution (such as toluene) and can be fabricated into a thin film applying to an OTFT via a spin-coating method in atmosphere environment.

Figure 2:
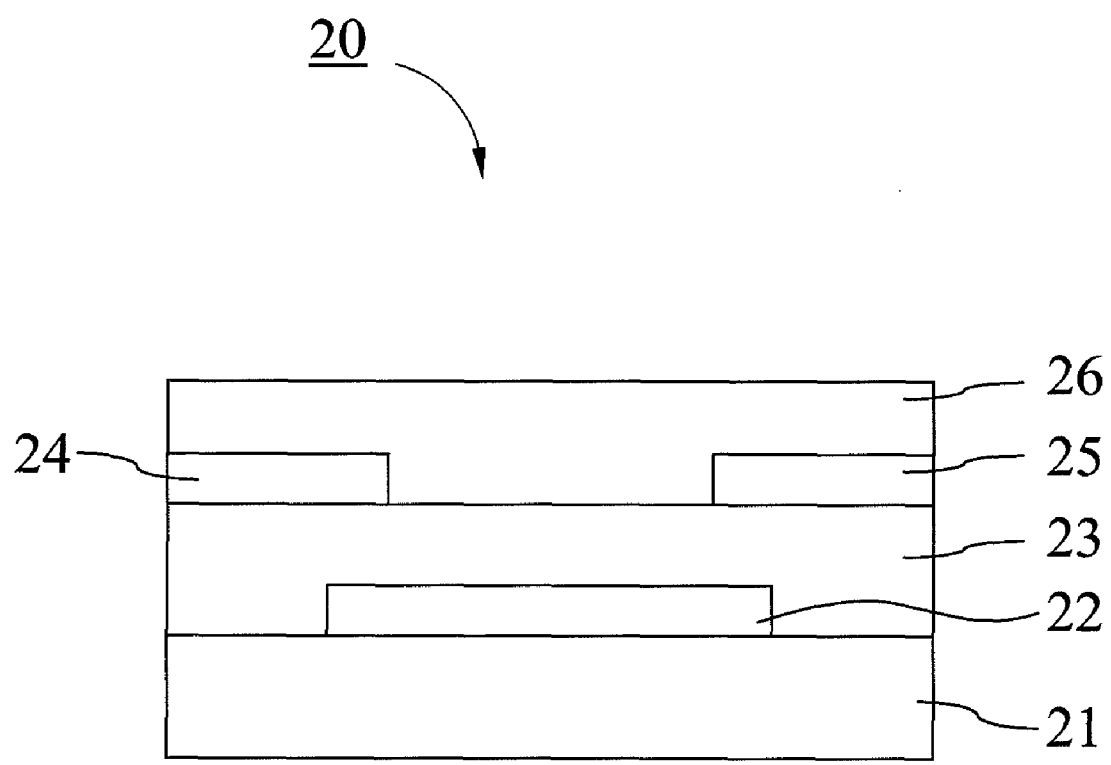
FIG. 2 is a diagram schematically showing that a PDI derivative applies to a BG-BC OTFT according to the present invention.
Figure 3:
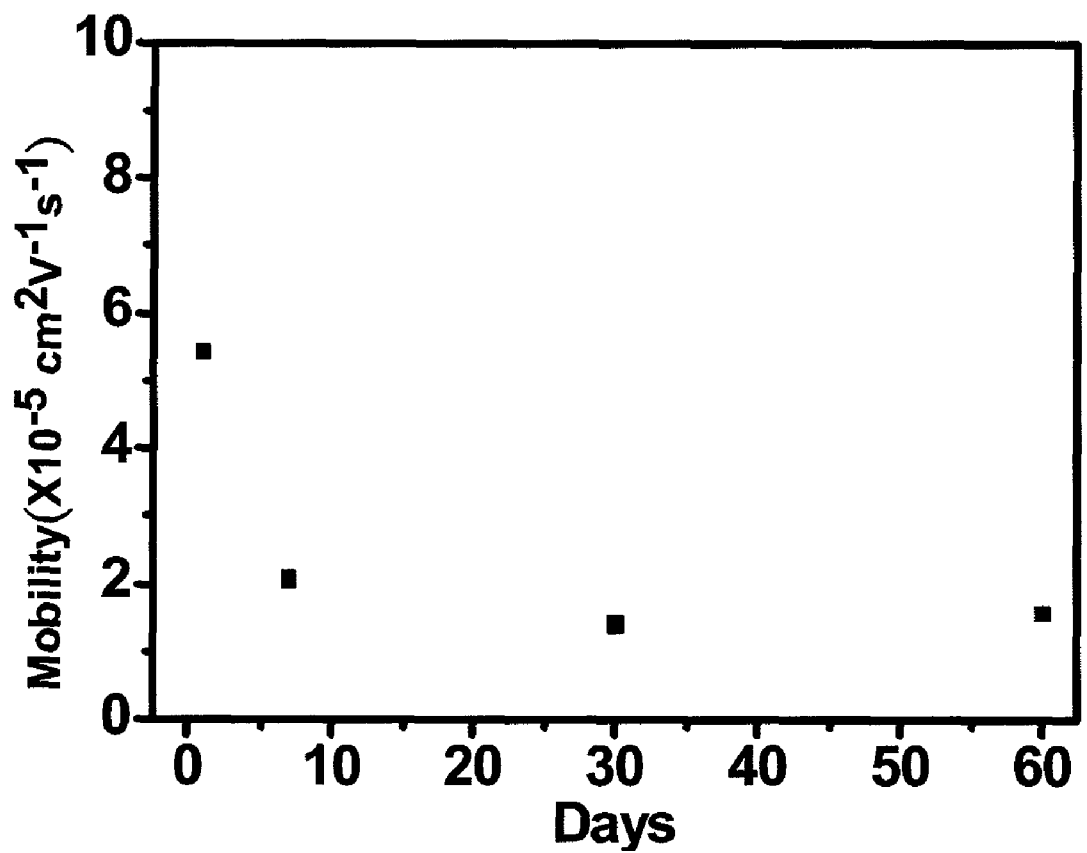
FIG. 3 is a diagram showing an experimental result proving that a PDI derivative of the present invention has air-stability.

Refer to FIG. 1 and FIG. 2 for diagrams respectively schematically showing a BG-TC (Bottom Gate-Top Contact) OTFT and a BG-BC (Bottom Gate-Bottom Contact) OTFT. The BG-TC OTFT 10 has a substrate 11, a gate 12 formed on the substrate 11, a dielectric layer 13 formed on the gate 12, a source 14 and a drain 15 formed over the dielectric layer 13, and an organic semiconductor layer 16 for conducting the source 14 and the drain 15. The BG-BC OTFT 20 has a substrate 21, a gate 22 formed on the substrate 21, a dielectric layer 23 formed on the gate 22, a source 24 and a drain 25 formed on the dielectric layer 23, and an organic semiconductor layer 26 for conducting the source 24 and the drain 25. In one embodiment, the organic semiconductor layers 16 and 26 are fabricated with a soluble process in the atmospheric environment. In one embodiment, the dielectric layers 13 and 23 respectively formed on the substrates 11 and 21 also are fabricated with a soluble process. For example, a liquid-phase deposited silicon dioxide (LPD-SiO2) is formed on a silicon substrate 11 or 21 to function as the dielectric layer 13 or 23, whereby the electron mobility thereof can reach 0.26 $cm^2V^{-1}s^{-1}$. Refer to FIG. 3 for a diagram showing the relationship of the electron mobility of TC-PDA-F and the time of exposure to air. FIG. 3, it shows that the electron mobility of TC-PDA-F slightly decreases from $5.34\times10^{-5}$ $cm^2V^{-1}s^{-1}$ to $1.6\times10^{-5}$ $cm^2V^{-1}s^{-1}$ after it has been exposed to air for two months. It indicates that TC-PDA-F still keeps the characteristics of a transistor.

Compared with the N-type organic semiconductor materials disclosed in prior art, the perylene diimide derivative of the present invention has a better solubility. The PDI derivative of the present invention is not fabricated with a evaporation method having higher cost and more restricted conditions but can be fabricated into a thin film applying to the organic semiconductor element at a low temperature and under an atmospheric environment. Further, the PDI derivative of the present invention has better air-stability and favors the application and development of flexible materials in the future.

The embodiments described above are only to exemplify the present invention but not to limit the scope of the present invention. Any equivalent modification or variation according the specification or drawings of the present invention is to be also included within the scope of the present invention.

What is claimed is:

1. A perylene diimide derivative of a general formula:

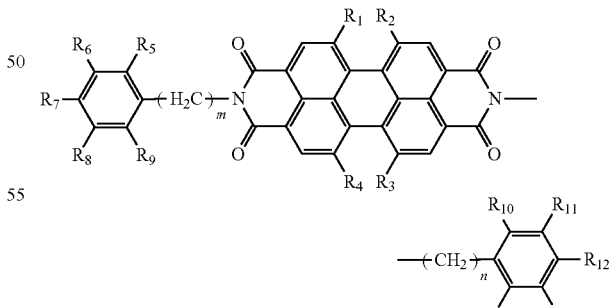

wherein m and n are respectively selected from integers 1-5 and independent to each other, and wherein $R_1$, $R_2$, $R_3$ and $R_4$ are respectively selected from an electron withdrawing group consisting of halogens, and a cyanogen group, and wherein $R_5$-$R_9$ and $R_{10}$-$R_{14}$, which are respectively at two ends of the molecule of the perylene diimide derivative, are independent to each other, and wherein one of $R_5$-$R_9$ is selected from a fluorine group, and wherein another one of $R_5$-$R_9$ is selected from a $C_1$-$C_{20}$ fluorinated alkyl group or a $C_1C_{20}$ perfluorinated alkyl group, and wherein the rest of $R_5$-$R_9$ are hydrogens, and wherein one of $R_{10}$-$R_{14}$ is selected from a fluorine group, and wherein another one of $R_{10}$-$R_{14}$ is selected from $C_1$-$C_{20}$ fluorinated alkyl group or $C_1$-$C_{20}$ perfluorinated alkyl group, and wherein the rest of $R_{10}$-$R_{14}$ are hydrogens, and wherein the perylene diimide derivative is soluble and has air-stability.

2. The perylene diimide derivative according to claim 1, wherein the electron withdrawing groups are selected from a group consisting of a fluorine group, a chlorine group, a bromine group, and a cyanogen group.

3. The perylene diimide derivative according to claim 1, wherein m equals to n.

4. The perylene diimide derivative according to claim 1, wherein $R_5$-$R_9$ and $R_{10}$-$R_{14}$ substituents are symmetric to each other.

5. The perylene diimide derivative according to claim 1, wherein $R_7$ and $R_{12}$ are hydrogen atoms.

6. The perylene diimide derivative according to claim 1 functioning as an organic semiconductor layer connecting to a source and a drain in an organic thin film transistor.

7. A perylene diimide derivative of a general formula:

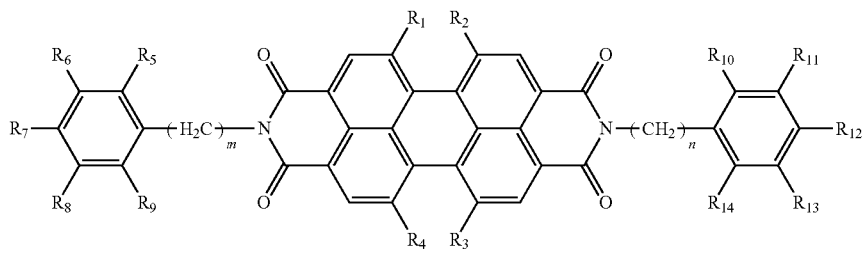

wherein m and n are respectively selected from integers 1-5 and independent to each other, and wherein $R_1$, $R_2$, $R_3$ and $R_4$ are respectively selected from an electron withdrawing group consisting of halogens, and a cyanogen group, and wherein $R_5$-$R_9$ and $R_{10}$-$R_{14}$, which are respectively at two ends of the molecule of the perylene diimide derivative, are independent to each other, and wherein at least two of $R_5$-$R_9$ are at meta positions, and wherein one of $R_5$-$R_9$ is selected from a fluorine group and wherein another one of $R_5$-$R_9$ is selected from a $C_1$-$C_{20}$ fluorinated alkyl group, or $C_1$-$C_{20}$ perfluorinated alkyl group and wherein the rest of $R_5$ $R_9$ are hydrogens, and wherein at least two of $R_{10}$-$R_{14}$ are at meta positions, and wherein one of $R_{10}$-$R_{14}$ is selected from a fluorine group and wherein another one is selected from a $C_1$-$C_{20}$ fluorinated alkyl group or a $C_1$-$C_{20}$ perfluorinated alkyl group, and wherein the rest of $R_{10}$-$R_{14}$ are hydrogens, and wherein the perylene diimide derivative is soluble and has air-stability.

8. The perylene diimide derivative according to claim 7, wherein the electron withdrawing groups are selected from a group consisting of a fluorine group, a chlorine group, a bromine group, and a cyanogen group.

9. The perylene diimide derivative according to claim 7, wherein m and n are 1.

10. The perylene diimide derivative according to claim 7, wherein $R_5$-$R_9$ and $R_{10}$-$R_{14}$ substituents are symmetric to each other.

11. The perylene diimide derivative according to claim 7, wherein $R_7$ and $R_{12}$ are hydrogen atoms.

12. The perylene diimide derivative according to claim 7 functioning as an organic semiconductor layer connecting to a source and a drain in an organic thin film transistor.

13. An organic semiconductor element comprising
a substrate;
a gate formed on the substrate;
a dielectric layer formed over the gate;
a source and a drain formed over the dielectric layer; and
an organic semiconductor layer connecting to the source and the drain,
wherein the organic semiconductor layer is made of a perylene diimide derivative including a chemical structure formula:

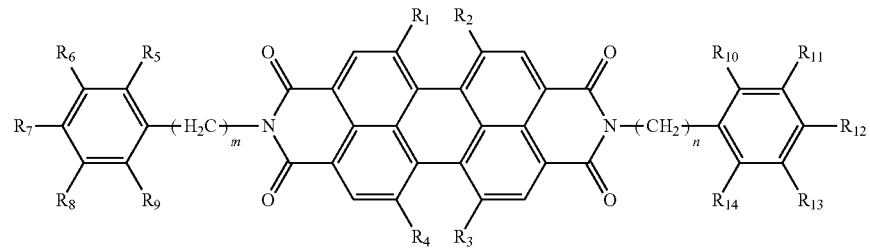

wherein m and n are respectively selected from integers 1-5 and
independent to each other, and wherein $R_1$, $R_2$, $R_3$ and $R_4$ are respectively selected from an electron withdrawing group consisting of halogens, and a cyanogen group, and wherein $R_5$-$R_9$ and $R_{10}$-$R_{14}$, which are respectively at two ends of the molecule of the perylene diimide derivative, are independent to each other, and wherein one of $R_5$-$R_9$ is selected from a fluorine group, and wherein another one of $R_5$-$R_9$ is selected from a $C_1$-$C_{20}$ fluorinated alkyl group or a $C_1$-$C_{20}$ perfluorinated alkyl group, and wherein the rest of $R_5$ $R_9$ are hydrogens, and wherein one of $R_{10}$-$R_{14}$ is selected from a fluorine group and wherein another one of $R_{10}$-$R_{14}$ is selected from a $C_1$-$C_{20}$ fluorinated alkyl group or a $C_1$-$C_{20}$ perfluorinated alkyl group, and wherein the rest of $R_{10}$-$R_{14}$ being hydrogens, and wherein the perylene diimide derivative is soluble and has air-stability.

14. The organic semiconductor element according to claim 13, wherein the substrate is made of silicon; the dielectric layer is made of a liquid-phase deposited silicon dioxide.

* * * * *